US012807615B2

(12) United States Patent
Selwood et al.

(10) Patent No.: US 12,807,615 B2

(45) Date of Patent: Nov. 24, 2026

(54) PREPARATION OF NEOSAXITOXIN

(71) Applicant: THE CAWTHRON INSTITUTE TRUST BOARD, Nelson (NZ)

(72) Inventors: Andrew Ian Selwood, Nelson (NZ); Roelof Van Ginkel, Upper Moutere (NZ); Craig Alan Waugh, Nelson (NZ)

(73) Assignee: THE CAWTHRON INSTITUTE TRUST BOARD, Nelson (NZ)

( * ) Notice: Subject to any disclaimer, the term of this patent is extended or adjusted under 35 U.S.C. 154(b) by 263 days.

(21) Appl. No.: 18/666,262

(22) Filed: May 16, 2024

(65) Prior Publication Data

US 2025/0019384 A1 Jan. 16, 2025

Related U.S. Application Data

(63) Continuation-in-part of application No. 17/914,515, filed on Sep. 26, 2022, which is a continuation-in-part of application No. PCT/IB2021/052506, filed on Mar. 26, 2021, application No. 18/666,262, filed on May 16, 2024 is a continuation of application No. 17/212,690, filed on Mar. 25, 2021, now Pat. No. 12,018,034, which is a continuation-in-part of application No. 17/018,816, filed on Sep. 11, 2020, now Pat. No. 11,028,094, which is a continuation of application No. 16/865,027, filed on May 1, 2020, now Pat. No. 10,822,344, which is a continuation-in-part of application No. PCT/IB2019/058019, filed on Sep. 23, 2019, and a continuation-in-part of application No. PCT/IB2018/057274, filed on Sep. 21, 2018.

(51) Int. Cl.
*C07D 487/14* (2006.01)

(52) U.S. Cl.
CPC .................................. *C07D 487/14* (2013.01)

(58) Field of Classification Search
CPC .................................................... C07D 487/14
See application file for complete search history.

(56) References Cited

U.S. PATENT DOCUMENTS

2023/0145895 A1 * 5/2023 Selwood .................. B01J 39/07
544/234

* cited by examiner

*Primary Examiner* — Erich A Leeser

(74) *Attorney, Agent, or Firm* — Thomas | Horstemeyer, LLP

(57) ABSTRACT

Semisynthetic methods of preparing neosaxitoxin of a purity and quantity sufficient to enable its use as an active pharmaceutical ingredient are disclosed. The scalable methods comprise the reductive desulfonation of an unresolved mixture of either toxin C3 and toxin C4 (C3,4) or gonyautoxin 1 and gonyautoxin 4 (GTX1,4) using dithiol in a buffered reaction solvent at a pH of about 7.5. The purification of the paralytic shellfish toxins (PSTs) from extracts of cultures of the dinoflagellates *Alexandrium pacificum* and *Gymnodinium catenatum* is disclosed.

3 Claims, 4 Drawing Sheets

PREPARATION OF NEOSAXITOXIN

CROSS REFERENCE TO RELATED APPLICATIONS

This application is a continuation-in-part of application Ser. No. 17/212,690, filed Mar. 25, 2021, which is a continuation-in-part of application Ser. No. 17/018,816, filed on Sep. 11, 2020, now U.S. Pat. No. 11,028,094, which is a continuation of application Ser. No. 16/865,027, filed on May 1, 2020, now U.S. Pat. No. 10,822,344, which is a continuation-in-part of application No. PCT/IB2019/058019, filed on Sep. 23, 2019, and a continuation-in-part of application No. PCT/IB2018/057274, filed on Sep. 21, 2018, and which claims priority to AU application No. 2020900916, filed on Mar. 25, 2020, all of which are hereby incorporated by reference in their entireties. This application is also a continuation in part of application Ser. No. 17/914,515, filed Sep. 26, 2022, which is a continuation in part of application No. PCT/IB2012/052506, filed May 18, 2012.

TECHNICAL FIELD

The invention relates to the semisynthetic preparation of neosaxitoxin from extracts of cultures of dinoflagellates such as *Alexandrium pacificum* and *Gymnodinium catenatum*. In particular, the invention relates to the semisynthetic preparation of neosaxitoxin comprising the reductive desulfonation of C3,4 or GTX1,4 purified from such extracts.

BACKGROUND ART

As stated in the publication of Garcia-Altares (2017), marine microalgal toxins constitute one of the most diverse and sophisticated groups of natural products. Examples are paralytic shellfish toxins (PSTs) such as saxitoxin (STX), its analogs and derivatives. Gonyautoxins (GTXs) are sulphated analogs of STX and marine bacteria can transform GTXs into STX through reductive eliminations. Toxins C3 and C4 are N-sulfocarbamoyl analogs of gonyautoxins 1 (GTX1) and 4 (GTX4). In marine environments the main producers of STX are eukaryotic dinoflagellates.

STX is a monoterpenoid indole alkaloid containing a tricyclic 3,4-propinoperhydropurine system with 2 guanidinium moieties formed by the $NH_2$ groups in the positions C2 and C8 of the reduced purine:

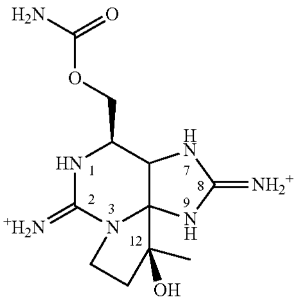 [SMILES: C[C@]1(O)CCN2C(=[NH2+])N[C@@H](COC(N)=O)C3NC(=[NH2+])NC321]

STX blocks voltage-gated sodium channels (VGSCs), but also binds to calcium and potassium channels. The nature of the substituents greatly influences the overall toxicity of saxitoxin analogs. The hydroxylation of N1, e.g. as in neosaxitoxin (neoSTX), does not play a major role in binding affinity, but seems to increase potency.

The prior art is replete with disclosures of the cosmetic and therapeutic applications of PSTs, including their use as local anaesthetics and analgesics. The publication of Mezher (2018) discloses that the US Food and Drug Administration (FDA) plans to develop guidance documents to encourage the development of extended-release local anaesthetics which could replace the need for systemic oral opioids in certain situations. The expectations of the US FDA are for the development of new non-opioid drugs to treat chronic pain that could provide a safer alternative for patients who require long-term use of analgesic drugs. The publications of Kohane et al (2000), Rogriguez-Navarro et al (2011), Templin et al (2015) and Wylie et al (2012) disclose the use of neoSTX in these applications. A limitation on the exploitation and widespread adoption of these applications is the availability of the PSTs in sufficient quantity and of sufficient purity to render their use in the manufacture of pharmaceutical preparations commercially viable.

The following publications include disclosures of the preparation of gonyautoxin 1 (GTX1), gonyautoxin 4 (GTX4) or neosaxitoxin (neoSTX). Often the preparation is on an analytical scale or does not provide the quantity and purity required for use of the preparation as an active pharmaceutical ingredient (API).

The publication of Hall et al (1984) discloses the confirmation by x-ray crystallography of the position and identity of the three substituents which, with the parent compound, form the array of twelve saxitoxins found in protogonyaulax.

The publication of Daigo et al (1985) discloses the extraction and isolation of neosaxitoxin (neoSTX) from specimens of crab. The dose-death time curve obtained for the isolated neoSTX was clearly distinguishable from the curve for saxitoxin (STX).

The publication of Laycock et al (1994) discloses methods for the purification of some of the common paralytic shellfish poisoning (PSP) toxins in quantities sufficient for use as analytical standards. The PSP toxins were purified from the dinoflagellate *Alexandrium excavatum*, the giant sea scallop (*Plagopecten magellanicus*) hepatopancreas and the cyanobacterium *Aphanizomenon flos-aquae*.

The publication of Laycock et al (1995) discloses conditions asserted to be optimal for the preparation of some paralytic shellfish poisoning (PSP) toxins. The objective of the studies disclosed is to provide analytical standards that may not be readily obtainable from natural sources. Reductive cleavage of the C-11 sulfate (desulfonation) of gonyautoxins is disclosed using dithiothreitol (DTT). Dithiothreitol (100 mM) in aqueous solution at pH 8.5 is disclosed to rapidly converted GTX2,3 to saxitoxin and GTX1,4 to neosaxitoxin.

The publication of Ravn et al (1995) discloses what are asserted to be optimal conditions for extraction of paralytic shellfish toxins from a clone of *Alexandrium tamarense*. The paralytic shellfish toxins are extracted with acetic acid and hydrochloric acid in the concentration range 0.01 to 1.0 N. Concentrations of hydrochloric acid in the range 0.03 to 1.0 N were observed to cause the amount of C1 and C2 toxins to decrease sharply with a concomitant increase in the amount of gonyautoxins 2 (GTX2) and 3 (GTX3).

The publication of Tsai et al (1997) discloses the detection of paralytic toxicity by a tetrodotoxin bioassay in specimens of crab. Partial purification and characterisation of the toxins demonstrated the main toxin to be tetrodotoxin with minor amounts of gonyautoxins (GTXs) and neosaxitoxin (neoSTX).

The publication of Siu et al (1997) discloses the examination of the effects of environmental and nutritional factors on population dynamics and toxin production in *Alexandrium catenella*. Optimum conditions for the growth of this species of dinoflagellate are disclosed along with the toxin profile for a species grown under these conditions. The toxin profile as detected by HPLC was found to include in descending order GTX4, GTX3, GTX1, B2, neosaxitoxin (neoSTX) and saxitoxin (STX).

The publication of Sato et al (2000) discloses the transformation of the O-sulfate group of GTX1 and GTX4 to methylene to form neosaxitoxin. The transformation was achieved using thiols such as glutathione and intermediates of the conversion were isolated.

The publication of Suzuki et al (2014) discloses the preparation of GTX1,4 from large algal cultures of an isolate of *Alexandrium tamarense*. This isolate (OF-23) is reported to produce a high proportion of GTX1,4 in the absence of C1,2. The conversion of GTX1,4 to neosaxitoxin was performed using 1% dithiothreitol (DTT) in 1% aqueous ammonium bicarbonate ($NH_4HCO_3$) at 50 °C for 1 hour. Neosaxitoxin is asserted to be chemically converted from GTX1,4 with a high recovery.

The publication of Parker et al (2002) discloses an investigation of the autotrophic growth of the toxic dinoflagellate, *Alexandrium minutum*, in three different high biomass culture systems, assessing growth, productivity and toxin production. The organism was grown in aerated and non-aerated two litre Erlenmeyer flasks, 0.5 litre glass aerated tubes, and a four-litre lab scale alveolar panel photobioreactor. A marked increase in biomass and productivity in response to aeration was observed. A maximum cell concentration of $3.3\times10^5$ cells/mL, a mean productivity of $0.4\times10^4$ cells/mL/day and toxin production of approximately 20 μg/L/day with weekly harvesting was reported.

The publication of Baker et al (2003) discloses the production by bacterial strains isolated from saxitoxin-producing dinoflagellates of compounds that could easily be mistaken for gonyautoxin 4 (GTX4).

The publication of Miao et al (2004) discloses the isolation of gonyautoxins (GTX1, GTX2, GTX3 and GTX4) from two strains of *Alexandrium minutum* Halim. The strain of *Alexandrium minutum* Halim designated Amtk4 is asserted to be suitable for the preparation of gonyautoxins.

The publication of Jiang and Jiang (2008) discloses the establishment of optimal conditions for the extraction of paralytic shellfish poisoning toxins from the gonad of *Chlamys nobilis*. The extraction uses acetic acid and hydrochloric acid in the concentration range of 0.04 to 1.0 mol/L. The use of hydrochloric acid in the concentration range of 0.25 to 1.0 mol/L was shown to cause a significant decrease of the toxins C1, C2 and GTX5 and the concomitant increase in the toxins GTX2,3. The amount of the three unstable toxins did not show any change when acetic acid was used in the extraction.

The publication of Liu et al (2010) discloses the culture of toxin producing *Alexandrium catenella* in the laboratory. A maximum cell density of $0.4\times10^4$ cells/mL was obtained within eight days of culture. Analysis by high performance liquid chromatograph (HPLC) of a crude extraction showed the major toxic components to be C1/2, GTX4, GTX5 and neoSTX at concentrations of about 0.04550, 0.2526, 0.3392, 0.8275 and 0.1266 μmol/L, respectively.

The publication of Foss et al (2012) discloses a comparison of extraction methods for paralytic shellfish toxins (PSTs) from the filamentous cyanobacterium *Lyngbya wollei*. In the absence of commercially available standards for the unique toxins produced by this cyanobacterium it was not possibly to quantify the toxins extracted.

The publication of Li et al (2013) discloses a method for the rapid screening and identification of paralytic shellfish poisoning (PSP) toxins in red tide algae. The method utilises hydrophilic interaction chromatography-high resolution mass spectrometry (HILIC-HR-MS) combined with an accurate mass database. Limits of detection (LOD) of ten common PSP compounds were in the range of 10 to 80 nmol/L. The developed method was asserted to be a useful tool for the rapid screening and qualitative identification of common PSP toxins in harmful algae.

The publication of Bernardi Bif et al (2013) discloses the sensitivity of sea urchins to toxic cell extracts containing saxitoxins.

The publication of Poyer et al (2015) discloses the development of an analytical method to characterise and differentiate saxitoxin analogs, including sulfated (gonyautoxins) and non-sulfated analogs. Hydrophilic interaction liquid chromatography (HILIC) was used to separate sulfated analogs. Ion mobility mass spectrometry (IM-MS) was used as a new dimension of separation based on ion gas phase confirmation to differentiate the saxitoxin analogs. Positive and negative ionisation modes were used for gonyautoxins. Positive ionisation mode was used for non-sulfated analogs. The coupling of three complementary techniques, HILIC-IM-MS, permitted the separation and identification of saxitoxin analogs, isomer differentiation being achieved in the HILIC dimension with non-sulfated analogs separated in the IM-MS dimension.

The publication of Rubio et al (2015) discloses a method to purify saxitoxin using a liquid chromatography methodology based on ionic pairs. The saxitoxin is extracted using hydrochloric acid and treated with ammonium sulfate following a treatment with trichloroacetic acid and hexane/diethyl ether (97/3). Samples were analysed by a semi-preparative HPLC in order to collect pure fractions of saxitoxin and these fractions were eluted in solid-phase cationic interchange STX extraction columns. The purified saxitoxin was reported to be stable and homogenous and its identity confirmed by LC-MS-MS. Analogs such as neosaxitoxin of a decarbamoyl saxitoxin were reported to be absent from the purified saxitoxin.

The publication of Chen et al (2016) discloses the application of serial coupling of reverse-phase liquid chromatography (RPLC) and hydrophilic interaction chromatography (HILIC) combined with high resolution mass spectrometry (HR-MS) to the simultaneous screening and identification of known lipophilic and hydrophilic toxins in the algae of harmful algal blooms (HABs). Lipophilic and hydrophilic toxins were extracted simultaneously by the use of ultrasound-assisted extraction (UAE). The publication demonstrated that HPLC/HILIC-HR-MS combined with an accurate mass list of known marine algal toxins may be used as a powerful tool for screening of different classes of known toxins in marine harmful algae.

The publication of Cho et al (2016) discloses the analysis of crude extracts of toxin-producing dinoflagellates by column switching and two-step gradient elusion using hydrophilic-interaction chromatograph (HILIC) combined with mass spectrometry. The publication states that the data obtained supports the hypothesis that the early stages of the saxitoxin biosynthesis and shunt pathways are the same in dinoflagellates and cyanobacteria.

The publication of Beach et al (2018) discloses the sensitive multiclass analysis of paralytic shellfish toxins, tetrodotoxins and domoic acid in seafood using a capillary electrophoresis (CE)-tandem mass spectrometry (MS/MS) method. A novel, highly acidic background electrolyte comprising 5 M formic acid was used to maximise protonation of analytes and is asserted to be generally applicable to simultaneous analysis of other classes of small, polar molecules with differing pka values.

The publication of Kellmann and Neilan (2007) proposes the fermentative production of neosaxitoxin and its analogs in recombinant *Escherichia coli* strains.

The publications of Lagos Gonzáles (2010, 2015a, 2015b and 2016) disclose the purification of phycotoxins from cyanobacteria produced in a continuous culture. The phycotoxins are isolated primarily from the bacteria but can also be isolated from the culture medium. In one embodiment of the process disclosed only neosaxitoxin (neoSTX) and saxitoxin (STX) are produced. In another embodiment of the process disclosed only gonyautoxin 2 (GTX2) and gonyautoxin 3 (GTX3) are produced.

The publication of Wang et al (2010) discloses the preparation of a paralytic shellfish poison (PSP) standard solution. The standard solution is prepared by removing impurities from shellfish material, collecting shellfish meat, adding distilled water and 0.1-0.3 mol/L hydrochloric acid solution, regulating pH to 1.5 to 5.0, and homogenising to obtain homogenate, precooling at −20 °C for 30 minutes to 24 hours, and lyophilising to obtain a core sample, grinding, and sieving, precooling at −20 °C for 10 minutes to six hours and lyophilising to obtain the standard sample. The method of preparation is asserted to have the advantages of low raw material cost and a simple preparation process.

The publication of Xiong and Qiu (2009) discloses the application of biguanido purine derivatives and their salts and esters for improving the therapeutic effect and reducing the side effects of antitumor agents. The biguanido purine derivates are saxitoxin analogs.

It is an object of the invention to provide neosaxitoxin in sufficient quantity and at sufficient purity to enable its use as an active pharmaceutical ingredient (API). It is an object of the invention to provide methods for the preparation of C3,4 or GTX1,4 or GTX6 in sufficient quantities and at sufficient purities to enable the preparation of the API. It is an object of the invention to provide semisynthetic methods of preparing the API from C3,4 or GTX1,4 or GTX6. These objects are to be read in the alternative with each other and the object to at least provide a useful choice in the selection of such methods.

SUMMARY OF INVENTION

In a first aspect a method of preparing a volume of concentrated aqueous extract for use in the preparation of a quantity of GTX1,4 is described, the method comprising:

1. Culturing a selected isolate of a dinoflagellate in a vertical column of aerated amended seawater for a period of time and at a temperature sufficient to provide a culture having a predetermined cell density;
2. Harvesting the cells from the culture having the predetermined cell density to provide a quantity of cellular biomass;
3. Resuspending the quantity of cellular biomass in an aqueous solution of a weak organic acid for a period of time and at a temperature sufficient to provide a mixture of residual biomass and an extract in solution;
4. Separating the residual biomass from the extract in solution; and then
5. Reducing the volume of the extract in solution to provide the volume of concentrated aqueous extract, where the selected isolate has been selected to produce a ratio of GTX2,3 to GTX1,4 of less than 0.1, the amended seawater is seawater amended with a nutrient medium, and the predetermined cell density is in the range $7\times10^4$ to $10^5$ cells/mL.

In a first embodiment the selected isolate is an isolate of the dinoflagellate *Alexandrium pacificum*. The isolate may be an isolate of the dinoflagellate *Alexandrium pacificum* that produces a ratio of GTX2,3 to GTX1,4 of less than 0.01. The isolate may be the isolate of the dinoflagellate *Alexandrium pacificum* designated CAWD234.

In a second embodiment the selected isolate is an isolate of the dinoflagellate *Gymnodinium catenatum*. The isolate of *Gymnodinium catenatum* may be an isolate selected from the group of isolates consisting of: *Gymnodinium catenatum* CAWD101; *Gymnodinium catenatum* CAWD102; and *Gymnodinium catenatum* CAWD126. The isolate of *Gymnodinium catenatum* may be the isolate designated CAWD102.

The nutrient medium may comprise nitrates, phosphates, trace metals and vitamins. The aqueous solution of a weak organic acid may be 0.25 to 0.75% acetic acid. The volume of concentrated aqueous extract may have a density between 1.06 to 1.14 g/mL.

In a second aspect a method of fractionating a volume of concentrated aqueous extract to provide a solution of partially purified GXT1, 4 is described, the method comprising:

1. Reducing the volume of the aqueous extract by ultrafiltration to provide a reduced volume;
2. Loading the reduced volume on a column of activated carbon sorbent to provide a loaded column; and
3. Eluting the loaded column with a stepwise gradient of water followed by aqueous acetic acid/acetonitrile to provide the solution of partially purified GTX1,4, where the volume of concentrated aqueous extract is an extract of a culture of a dinoflagellate. The volume of concentrated aqueous extract may be an extract of a culture of a dinoflagellate prepared according to the method described as the first aspect.

In a third aspect a method of preparing a quantity of neoSTX is described, the method comprising contacting in solution in a buffered reaction solvent a quantity of GTX1,4 and a quantity of dithiol for a period of time and at a temperature sufficient to provide a conversion product in which greater than 97.5% (w/w) of the GTX1,4 has been converted to neoSTX.

The quantity of GTX1,4 is typically of a purity of at least 97.58 (w/w). The quantity of GTX1,4 may be of a purity of at least 98.75% (w/w) or at least 998 (w/w). The pH of the solution is in the range 7.2 to 7.8 and may be in the range 7.4 to 7.6. The buffered reaction solvent may be buffered aqueous acetic acid. The dithiol may be selected from the group consisting of dithiothreitol (DTT) and dithiobutylamine (DTBA). In an embodiment the dithiol is dithiothreitol (DTT).

The conversion product may be applied to a silica based weak cation exchange sorbent and eluted with an aqueous weak acid to separate the neoSTX from the dithiol and provide the quantity of neoSTX. The aqueous weak acid may be an aqueous weak organic acid, such as aqueous acetic acid.

The quantity of neoSTX may be greater than 100 mg with a purity greater than 99.5% (w/w). The method of preparing the quantity of neoSTX may be a near quantitative method.

In a fourth aspect a method of preparing a quantity of GTX1,4 is provided, the method comprising subjecting a C3,4 containing extract of a culture of an isolate of *Gym-*

*nodinium catenatum* to acid hydrolysis to provide a hydrolysate where greater than 508 of the C3,4 has been converted to GTX1,4.

The subjecting the C3,4 containing extract of a culture of an isolate of *Gymnodinium catenatum* to acid hydrolysis may be by diluting the C3,4 containing extract with acid to provide a final concentration of 0.5 to 0.2N acid. The subjecting the C3,4 containing extract of a culture of an isolate of *Gymnodinium catenatum* to acid hydrolysis may be by diluting the C3,4 containing extract with acid to provide a final concentration of 0.1N acid. The acid may be a strong acid. The acid may be hydrochloric acid. Greater than 70% of the C3,4 may be converted to GTX1,4. Greater than 90% of the C3, 4 may be converted to GTX1,4. Greater than 95% of the C3,4 may be converted to GTX1,4.

The isolate of *Gymnodinium catenatum* may be an isolate selected from the group of isolates consisting of: *Gymnodinium catenatum* CAWD101; *Gymnodinium catenatum* CAWD102; and *Gymnodinium catenatum* CAWD126. The isolate of *Gymnodinium catenatum* may be the isolate designated CAWD102.

The method may comprise the step of isolating the GTX1,4 from the hydrolysate to provide the quantity of purified GTX1,4 where the hydrolysate is subjected to crossflow ultrafiltration before being applied to a sorbent. The hydrolysate may be neutralised before being subjected to crossflow ultrafiltration. The hydrolysate may be neutralised with ammonium hydroxide.

In a fifth aspect a method of preparing a quantity of neoSTX is provided, the method comprising:

1. subjecting a C3,4 containing extract of a culture of an isolate of *Gymnodinium catenatum* to acid hydrolysis to provide a hydrolysate where greater than 50% of the C3,4 has been converted to GTX1,4;
2. isolating the GTX1,4 from the hydrolysate to provide a quantity of purified GTX1,4; and then
3. contacting in a solution in a buffered reaction solvent the quantity of purified GTX1,4 and a quantity of dithiol to provide a reaction product in which greater than 97.5% (w/w) of the purified GTX1,4 has been converted to neoSTX.

The subjecting the C3,4 containing extract of a culture of an isolate of *Gymnodinium catenatum* to acid hydrolysis may be by diluting the C3,4 containing extract with acid to provide a final concentration of 0.5 to 0.2N acid. The subjecting the C3,4 containing extract of a culture of an isolate of *Gymnodinium catenatum* to acid hydrolysis may be by diluting the C3,4 containing extract with acid to provide a final concentration of 0.1N acid. The acid may be a strong acid. The acid may be hydrochloric acid. Greater than 70% of the C3,4 may be converted to GTX1,4. Greater than 90% of the C3,4 may be converted to GTX1,4. Greater than 95% of the C3,4 may be converted to GTX1,4.

The isolating the GTX1,4 may include subjecting the hydrolysate to crossflow ultrafiltration before applying to a sorbent. The method may comprise the step of neutralising the hydrolysate before subjecting the hydrolysate to crossflow ultrafiltration. The hydrolysate may be neutralised with ammonium hydroxide.

The method may comprise the step of applying the reaction product to a silica based weak cation exchange sorbent and eluting with an aqueous weak acid to separate the neoSTX from the dithiol and provide the quantity of neoSTX. The aqueous weak acid may be an aqueous weak organic acid. The buffered reaction solvent may be buffered aqueous acetic acid.

The solution has a pH in the range 7.2 to 7.8. The solution may have a pH in the range 7.4 to 7.6. The solution may have a pH of about 7.5.

The quantity of neoSTX may be greater than 100 mg and may have a purity greater than 99.5% (w/w).

In a sixth aspect a method of preparing a quantity of neosaxitoxin is provided, the method comprising:

1. purifying a quantity of C3,4 from an extract of a culture of an isolate of *Gymnodinium catenatum;*
2. contacting in a solution in a reaction solvent the quantity of purified C3,4 and a quantity of dithiol at a temperature and for a time sufficient to provide a reaction product in which greater than 97.5% (w/w) of the purified C3,4 has been converted to GTX6; and then
3. subjecting the reaction product to mild acid hydrolysis to provide the quantity of neosaxitoxin.

Preferably, the reaction solvent is a buffered reaction solvent.

Preferably, the method comprises applying the reaction product to a silica based weak cation exchange sorbent and eluting with an aqueous weak acid to separate the GTX6 from the dithiol and provide a quantity of GTX6 and then subjecting the quantity of GTX6 to mild acid hydrolysis to provide the quantity of neosaxitoxin. More preferably, the aqueous weak acid is an aqueous weak organic acid.

Preferably, the reaction solvent is buffered aqueous acetic acid.

Preferably, the solution has a pH in the range 7.2 to 7.8. More preferably, the solution has a pH in the range 7.4 to 7.6. Most preferably, the solution has a pH of 7.5.

Preferably, the mild hydrolysis is by contacting the GTX6 with a dilute strong acid and heating to a temperature for a period of time sufficient to convert greater than 90% (w/w) of the GTX6 to neosaxitoxin. More preferably, the strong acid is hydrochloric acid. Preferably, the temperature is 80 °C±2 °C. Preferably, the time is at least 30 minutes.

Preferably, the isolate of *Gymnodinium catenatum* is an isolate selected from the group of isolates consisting of: *Gymnodinium catenatum* CAWD101; *Gymnodinium catenatum* CAWD102; and *Gymnodinium catenatum* CAWD126. More preferably, the isolate of *Gymnodinium catenatum* is the isolate designated CAWD102.

Preferably, the quantity of neosaxitoxin is greater than 100 mg and has a purity greater than 99.5% (w/w).

The foregoing methods are proposed for the batch preparation of GTX1,4 and neoSTX in quantities and of purities not previously obtainable (cf. Lagos Gonzáles (2010, 2015a, 2015b and 2016)).

In a seventh aspect a batch preparation of neosaxitoxin is provided where the quantity is greater than 100 mg and the purity is greater than 99.5% (w/w).

Preferably, the batch preparation comprises less than 0.004% (w/w) dithiothreitol (DTT) and no greater than 0.05 saxitoxin (STX).

In the description and claims of this specification the following abbreviations, acronyms, phrases and terms have the meaning provided: "batch preparation" means prepared discontinuously, produced at one time; "biosynthetic" means prepared within living organisms or cells; "CAS RN" means Chemical Abstracts Service (CAS, Columbus, Ohio) Registry Number; "comprising" means "including", "containing" or "characterized by" and does not exclude any additional element, ingredient or step; "consisting of" means excluding any element, ingredient or step not specified except for impurities and other incidentals; "consisting essentially of" means excluding any element, ingredient or step that is a material limitation; "dcNEO" means decarbamoylneosaxitoxin, i.e. (3aS,4R,10aS)-2-amino-3a,4,5,6,8,9-hexahydro-5-hydroxy-4-(hydroxymethyl)-6-imino-1H,10H-pyrrolo[1,2-c]purine-10,10-diol [CAS RN 68683-58-9]; "GTX" means gonyautoxin; "GTX1" means gonyautoxin 1, i.e. (3aS,4R,9R,10aS)-9-(hydrogen sulfate)-2-amino-4-[[(aminocarbonyl)oxy]methyl]-3a,4,5,6,8,9-hexahydro-5-hydroxy-6-imino-1H, 10H-pyrrolo [1,2-c]purine-9,10,10-triol [CAS RN 60748-39-2]; "GTX4" means gonyautoxin 4, i.e. (3aS,4R,9S,10aS)-9-(hydrogen sulfate)-2-amino-4-[[(aminocarbonyl)oxy]methyl]-3a,4,5,6,8,9-hexahydro-5-hydroxy-6-imino-1H,10H-pyrrolo[1,2-c]purine-9,10,10-triol [CAS RN 64296-26-0]; "GTX1,4" means an unresolved mixture (as solid or in solution) comprising gonyautoxin 1 and gonyautoxin 4; "GTX2,3" means an unresolved mixture (as solid or in solution) comprising gonyautoxin 2 and gonyautoxin 3; "near quantitative" means greater than 97.5% (w/w) of substrate, e.g. GTX1,4, is converted to product, e.g. neoSTX; "neoSTX" or "NEO" means neosaxitoxin, i.e. (3aS,4R,10aS)-2-amino-4-[[(aminocarbonyl)oxy]methyl]-3a,4,5,6,8,9-hexahydro-5-hydroxy-6-imino-1H,10H-pyrrolo[1,2-c]purine-10,10-diol [CAS RN 64296-20-4]; "nutrient medium" means a medium comprising trace metals and vitamins; "preparative scale" means prepared in batches of greater than 100 mg; "semi-synthetic" means prepared by chemical conversion of an enriched or at least partially purified biosynthetic precursor; "toxin C3" or "C3" means the C-[[(3aS,4R,9R,10aS)-2-amino-3a,4,5,6,9,10-hexahydro-5,10,10-trihydroxy-6-imino-9-(sulfooxy)-1H,8H-pyrrolo[1,2-c]purin-4-yl] methyl] ester of N-sulfocarbamic acid [CAS RN 89614-45-9]; and "toxin C4" or "C4" means the C-[[(3aS,4R,9S,10aS)-2-amino-3a,4,5,6,9,10-hexahydro-5,10,10-trihydroxy-6-imino-9-(sulfooxy)-1H,8H-pyrrolo[1,2-c]purin-4-yl]methyl] ester of N-sulfocarbamic acid [CAS RN 89674-98-6]. A paronym of any of the defined terms has a corresponding meaning.

The terms "first", "second", "third", etc. used with reference to aspects, elements, features or integers of the matter described in the Summary of Invention, or with reference to alternative embodiments, are not intended to imply an order of preference. Where concentrations or ratios of reagents are specified the concentration or ratio specified is the initial concentration or ratio of the reagents. Where a pH or pH range of a solution or reaction solvent is specified, the pH or pH range specified is the initial pH or pH range of the solution or reaction solvent. Where values are expressed to one or more decimal places standard rounding applies. For example, 1.7 encompasses the range 1.650 recurring to 1.749 recurring. Where there is any conflict or inconsistency between the structural representation of a compound and the full systematic name provided in this specification the structural representation shall take precedent unless a CAS RN is provided in conjunction with the systematic name in which case the structural representation provided in the Registry database (CAS, Columbus, Ohio) takes precedent. Purity of isolated GTX1,4 and the quantity of neoSTX is determined according to Method 3 [F. Analysis].

The methods will now be described in detail with reference to embodiments or examples and the figures of the accompanying drawings pages. Although the description is provided referencing specific embodiments or examples it should be appreciated that variations and modifications may be made to these specific embodiments or examples. Where known equivalents exist to specified elements, features or integers of the embodiments or examples, such equivalents are incorporated as if specifically referred to in the description. Variations and modifications to the embodiments or examples that include substitution of elements, features or integers described for equivalent elements, features or integers disclosed in and selected from the referenced publications are within the scope of the protection sought unless specifically excluded. The advantages provided by the methods described and discussed in the description may be provided in the alternative or in combination in different embodiments.

DESCRIPTION

Figure 1:
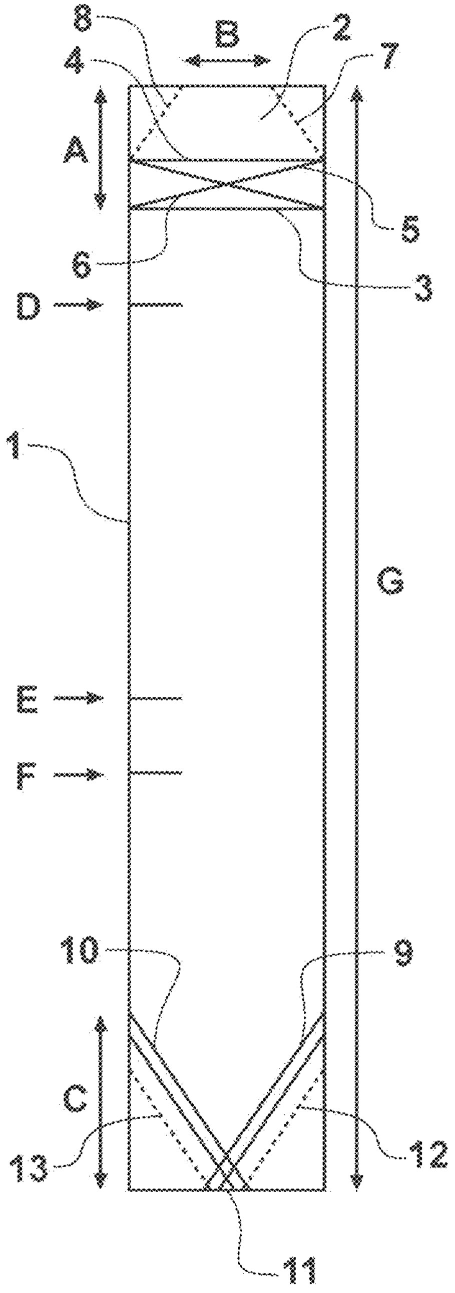
FIG. 1. A plan view of a hanging bag (1) formed from a length of tubular plastic for use in the bulk culture of isolates. Traversing single (3, 4, 5 and 6) and double solid lines (9 and 10) identify where two or more layers of the tubular plastic are heat welded together. Traversing broken lines identify where four (7 and 8) or two (12 and 13) layers of the tubular plastic are cut to provide a hanging loop (2) and cone, respectively.

According to the methods described a quantity of C3,4 or GTX1,4 or GTX6 is prepared either biosynthetically or semi-synthetically from a concentrated extract of a culture of an isolate of *Alexandrium pacificum* or an isolate of *Gymnodinium catenatum*.

Extracts of cultures of isolates of *Alexandrium pacificum* that produce relatively low amounts of gonyautoxin 2 (GTX2) and gonyautoxin 3 (GTX3) have been determined to be most suitable as a source for the purification of GTX1,4 from extracts of cultures of this species. Extracts of cultures of isolates of *Gymnodinium catenatum* that produce relatively high amounts of toxins C3 and C4, the N-sulfocarbamoyl derivatives of GTX1 and GTX4, may also be used following mild acid hydrolysis according to Scheme I. Toxins C3 and C4 may also be purified from the extracts of cultures of isolates of *Gymnodinium catenatum* and converted to GTX6 by reductive desulfonation using a dithiol as the reducing agent (Scheme II, step a). Mild acid hydrolysis of the intermediate GTX6 then yields neosaxitoxin (neoSTX) (Scheme II, step b) (Shimizu (1984)). Extracts of cultures of isolates of *Alexandrium pacificum* and *Gymnodinium catenatum* are available from the Cawthron Institute, Nelson, New Zealand.

The introduction of an ultrafiltration step prior to desalting has been found to be particularly advantageous when purifying C3,4 or GTX1,4 or GTX6 from these extracts. Without wishing to be bound by theory it is believed that ultrafiltration removes a substantial portion of the solutes that might otherwise interfere with the desalting step on sorbents such as activated carbon. The introduction of the ultrafiltration step thereby reduces the quantity of sorbent that would otherwise be required.

SCHEME I

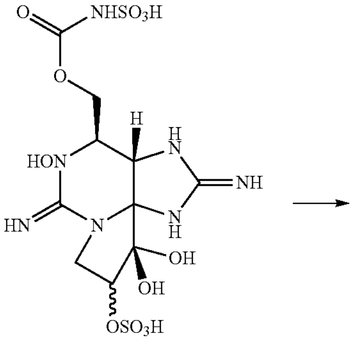

C3, 4

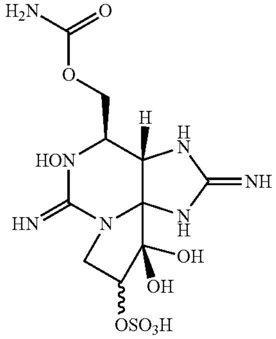

GTX1, 4

SCHEME II

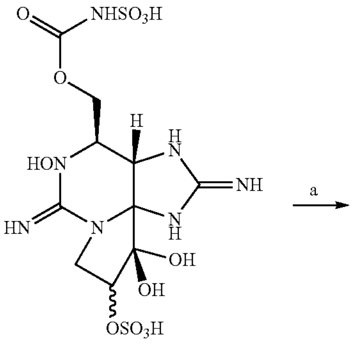

C3, 4

-continued

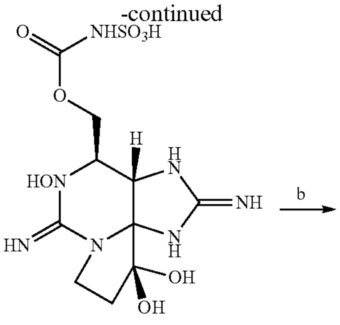

GTX6

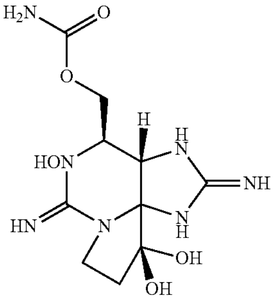

neoSTX

The publication of Laycock et al (1994) discloses the extraction and purification of GTX1 and GTX4 from hepatopancreas of scallops (*Placopecten magallanicus*):

Tissues (1 kg) were homogenized in 1 L of 0.1 M HCl using a Polytron tissue homogenizer, (Model PT10/35, Brinkman Instruments Canada Ltd, Rexdale, ON). The slurry was heated to 80 °C for 30 min, then cooled and centrifuged (5,000 g, 20 min) to remove precipitated protein. The supernatant fluid was extracted twice with dichloromethane (500 ml each). The aqueous layer was concentrated by rotary evaporation to 200 ml then poured onto a column (10 cm ID×15 cm) of a mixture of activated charcoal (Norite, A, 500 g, BDH Ltd.) and Celite (500 g, Johns-Manville). The column was washed with a solution of 20% ethanol and 1% acetic acid. Several one liter fractions were collected and toxin concentrations monitored by HPLC-FD. Toxin-containing fractions were concentrated by rotary evaporation and lyophilized.

The publication further discloses separation on Bio-Rex-70 was not complete for any of the gonyautoxins. However, by repeatedly removing GTX2 and re-equilibrating the mixture, the proportion of GTX2 and GTX3 contaminating the GTX1 and GTX4 fractions was gradually reduced.

The publication of Laycock et al (1995) discloses that dithiothreitol at a concentration of 100 mM in aqueous solution at pH 8.5 rapidly converted GTX1,4 to neoSTX and a small (less than 10%) amount of neosaxitoxinol (as determined by capillary electrophoresis). By contrast, it has now been determined that when performing the conversion at a preparative—as opposed to analytical—scale the optimum pH is lower and in the range 7.2 to 7.8, more specifically 7.4 to 7.6, when dithiothreitol (DTT) is used as the reducing agent. In general terms, purified GTX1,4 is converted to neoSTX in a solution buffered to a pH about 7.5 by reductive desulfonation using a dithiol as the reducing agent. The reductive desulfonation of GTX1,4 at a preparative scale is facilitated by the use of a buffered reaction solvent.

In solution, toxin C3 and toxin C4, and gonyautoxin 1 (GTX1) and gonyautoxin 4 (GTX4), exist as pairs of epimers. For the former pair of epimers, the conversion of toxin C4 to toxin C3 is favoured (Hall et al (1984)). For the latter pair of epimers, GTX1 is the thermodynamically most favoured. Epimerisation is believed to occur under most conditions via keto-enol equilibration at C-12.

In the first step of the proposed 2-step reaction mechanism according to SCHEME III a thiol group of the dithiol (R-SH) attacks the electrophilic C-12 of the keto form (I) to form a thiohemiketal (II). Conversion to a thioether (IV) occurs via an episulfonium ion intermediate (III) when the leaving group (O-sulfate) is oriented anti to the sulphur atom (as in the reactive epimer GTX1). In the second step of the proposed reaction mechanism the thiol group of the dithiol reacts with the sulphur of the thioether (IV) to form a disulfide thereby yielding an enolate that readily hydrates to GTX6 (Va) or neoSTX (Vb).

reducing agent. The use of dithiols such as dithiothreitol (DTT) and dithiobutylamine (DTBA) is preferred over the use of monothiols such as glutathione (GSH) and mercaptoethanol (ME) (cf. Sakamoto et al (2000) and Sato et al (2000)). Higher rates of conversion are obtained when using the dithiols, rendering them more suitable for use in the production of neoSTX on a preparative scale. Furthermore, the excess dithiol, sodium phosphate buffer and unreacted C3,4 or GTX1,4 may be most conveniently removed from the GTX 6 or neoSTX containing conversion product by the use of cation exchange chromatography. The silica based weak cation exchange sorbent Sepra™ WCX has been determined to be a suitable sorbent as it has been determined not to retain the dithiol DTT. Trials of the polymeric based weak cation exchange sorbent Strata-X™ CW (Phenomenex) determined this sorbent to be unsuitable for purification of neoSTX from the conversion product on a prepara-

SCHEME III

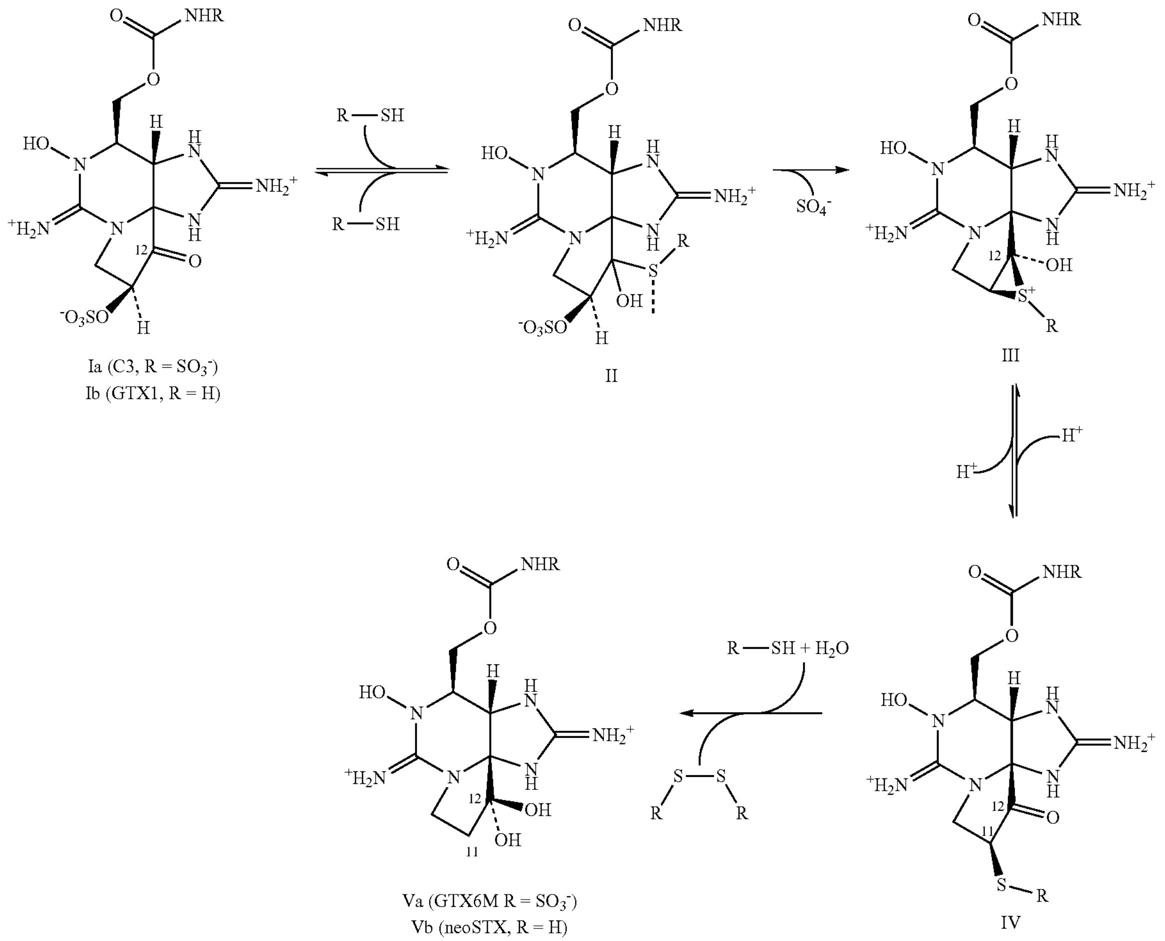

Ia (C3, R = $SO_3^-$)
Ib (GTX1, R = H)

II

III

IV

Va (GTX6M R = $SO_3^-$)
Vb (neoSTX, R = H)

As noted above in general terms the optimal pH for the conversion of C3,4 to GTX6 or GTX1,4 to neoSTX described in the following examples has been determined to be about 7.5 (cf. Laycock et al (1995)). Without wishing to be bound by theory it is believed that a pH in this range ensures both (i) an optimal rate of epimerisation between the gonyautoxin epimers and (ii) optimal degrees of electrophilicity at C-12 and deprotonation of the dithiol used as the tive scale. The excess dithiol is retained by both an ion exchange and a reverse phase mechanism when using this sorbent. Although a portion of the excess dithiol is eluted with organic solvents such as acetonitrile/water a further portion is eluted with 1 M acetic acid frustrating the purification of the neoSTX when using this sorbent. Similar observations are anticipated to be made when the product of the reductive desulfonation is GTX6

EXAMPLES

A. Materials 10 mM acetic acid (0.6 g/L in deionised water); amended seawater (7 mL/L L1 nutrient medium in seawater); deionised water (Milli-Q™, Merck-Millipore); IN hydrochloric acid (1N HCl); L1 nutrient medium (1.25 g/L EDTA, 0.91 g/L $FeCl_3 \cdot 6H_2O$, 0.29 mL/L trace metal stock solution, 21.6 g/L $NaNO_3$, 1.44 g/L $NaH_2PO_4$ and 14.4 mL/L vitamin stock solution); Mobile Phase A (2.2 g/L sodium heptane sulphonic acid (sodium salt) and 0.31 g/L 85% phosphoric acid adjusted to pH 7.1 with 25% ammonium hydroxide); Mobile Phase B (0.18 acid in acetonitrile); Mobile Phase C (0.18 acetic acid in deionised water); roll of tubular (230 mm×200 m×250 μm) low density poly (ethylene) (LDPE) plastic (Amcor Limited); seawater (30 to 37 ppt salinity); trace metal stock solution (2.5 g/L $CuSO_4 \cdot 5H_2O$, 20 g/L $Na_2MoO_4 \cdot 2H_2O$, 23 g/L $ZnSO_4 \cdot 7H_2O$, 11.9 g/L $CoCl_2 \cdot 6H_2O$, 178 g/L $MnCl_2 \cdot 4H_2O$, 1.3 g/L $H_2SeO_3$, 2.6 g/L $NiSO_4 \cdot 6H_2O$, 1.8 g/L $Na_3VO_4$ and 1.9 g/L $K_2CrO_4$); vitamin stock solution (0.01 g/L biotin, 2 g/L thiamine and 0.01 g/L vitamin B12). Vitamin stock solutions are filter sterilised and aseptically added through a 0.22 μm syringe filter during preparation of amended seawater following the autoclaving of other ingredients.

B. Inocula

Figure 2:
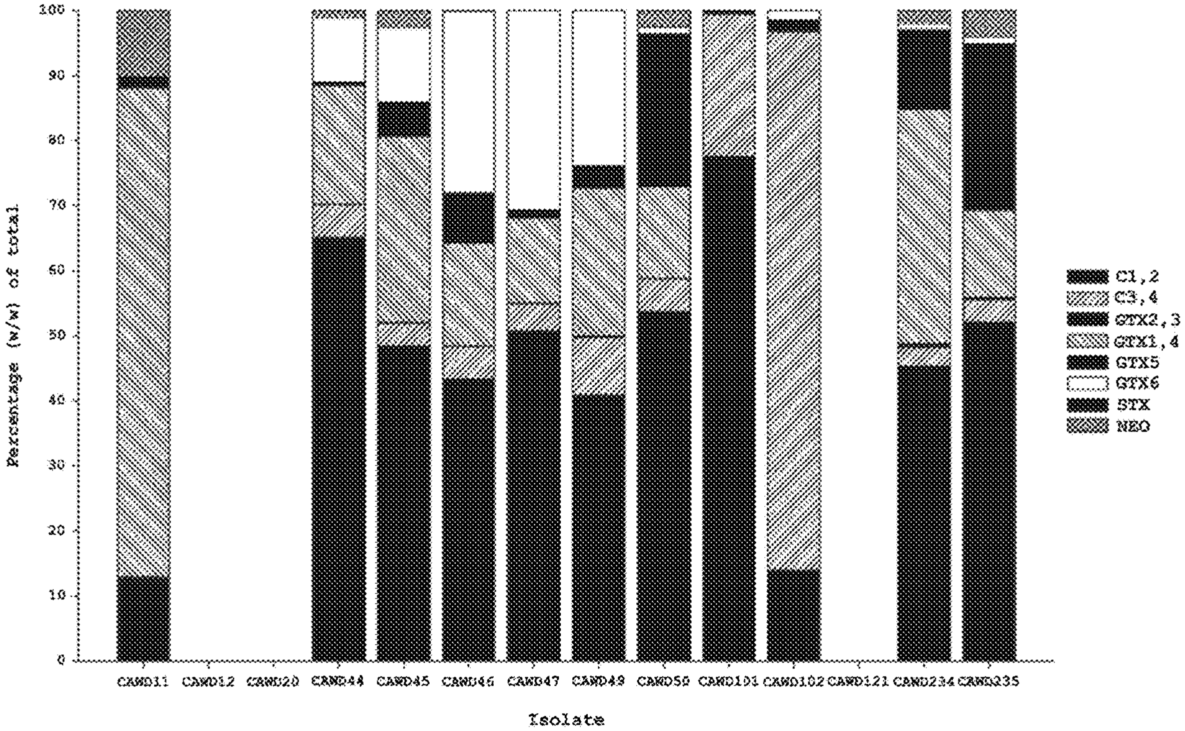
FIG. 2. The profiles of toxins produced by isolates of the species *Alexandrium minutum, Alexandrium ostenfeldii, Alexandrium pacificuma* and *Gymnodinium catenatum* (Table 1) when cultured in vertical columns of aerated amended sea water and extracted without mild acid hydrolysis. The isolates designated as CAWD12, CAWD20 and CAWD121 are identified as non-producers of toxins under these culture conditions.
Figure 3:
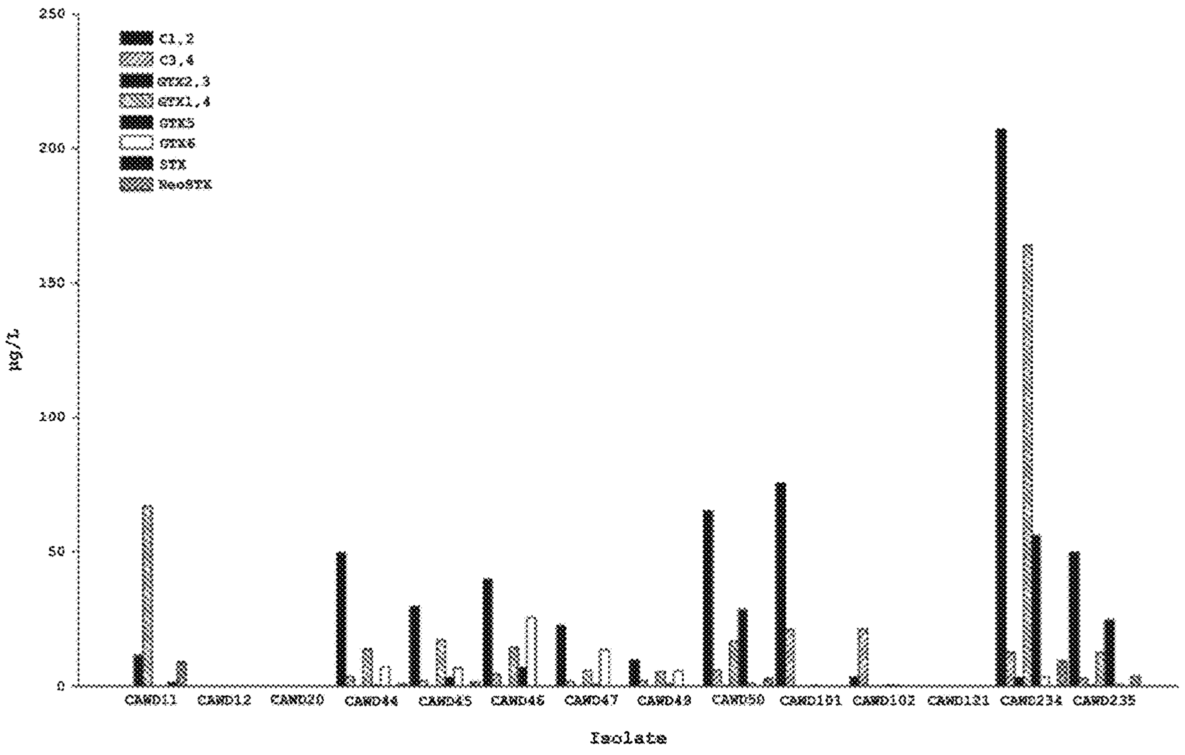
FIG. 3. Amounts of toxins determined to be produced by isolates of the species *Alexandrium minutum, Alexandrium ostenfeldii, Alexandrium pacificuma* and *Gymnodinium catenatum* (Table 1) when cultured in vertical columns of aerated amended sea water and extracted without mild acid hydrolysis.

Isolates are obtained from naturally occurring algal blooms in coastal waters. Species responsible for harmful algal blooms include *Alexandrium minutum, Alexandrium pacificum* (formerly referred to as *Alexandrium catenella*), *Alexandrium tamarense* and *Gymnodium catenatum*. Individual isolates have been evaluated for their production of toxins when cultured in bulk according to the following protocols. The concentrations of toxins detected in extracts of these cultures are provided in Table 1. The concentrations are expressed as picogram per cell and are determined for extracts that have not been subjected to mild acid hydrolysis. Representations of the structures of the toxins referred to in Table 1, FIG. 2 and FIG. 3 are provided below. The representations are of the structures of the toxins in their neutral (uncharged) form.

C. Culture

Individual isolates are cultured in aerated vertical columns of amended seawater in a plurality of hanging bags. The bags are hung in an incubation room maintained at a temperature of 16 to 20 °C. The bags are illuminated according to a 16-hour/8-hour light/dark cycle. Automated carbon dioxide ($CO_2$) dosing is used to maintain the pH in the range 8 to 9 during the light phase of the light/dark cycle. Standard personal protection equipment is worn by operators to minimise the risk of exposure to toxins.

Reference is made to FIG. 1 of the accompanying drawings pages where a plan view of a cut and welded hanging bag (1) for use in the bulk culture of isolates is provided. The bags are formed from a roll of tubular plastic by cutting and heat welding according to the following protocol.

After discarding the first two metres of a new roll of tubular plastic a 20 cm section is cut and the open ends of the excised section each sealed by a heat weld. The inner surfaces of the sealed section of tubular plastic roll are subjected to microbiological evaluation before the remainder of the new roll of tubular plastic is used for the fabrication of hanging bags.

TABLE 1

Concentration (pg/cell) of toxins detected in extracts of cultures of isolates of the species *Alexandrium minutum*, *Alexandrium pacificum*, *Alexandrium ostenfeldii* and *Gymnodinium catenatum*. Relatively high concentrations of C3, 4 or GTX1, 4 are emphasised [bold].

| Species | Designation | cells/ mL | GTX-1, 4 | C1, 2 | C3, 4 | dcGTX-2, 3 | GTX-2, 3 | GTX-5 | GTX-6 | dcSTX | dcNEO | STX | NEO |
|---|---|---|---|---|---|---|---|---|---|---|---|---|---|
| *A. minutum* | CAWD011 | 55035 | 3.1 | 0.01 | ND | 0.02 | 0.57 | 0.01 | ND | ND | ND | 0.39 | 0.33 |
| *A. minutum* | CAWD012 | 25961 | ND | ND | ND | ND | ND | ND | ND | 0.01 | ND | ND | ND |
| *A. pacificum* | CAWD044 | 5891 | 0.37 | 0.55 | 0.14 | 0.06 | 0 | 0.01 | 0.07 | 0 | 0 | 0 | 0.03 |
| *A. pacificum* | CAWD045 | 8004 | 0.59 | 0.67 | 0.13 | 0.04 | 0 | 0.19 | 0.15 | 0.01 | 0 | 0 | 0.18 |
| *A. pacificum* | CAWD046 | 5602 | 4.2 | 9.53 | 2.6 | 1.1 | 0.37 | 3 | 5.2 | 0.12 | ND | 0.12 | 0.21 |
| *A. pacificum* | CAWD047 | 7505 | 1.9 | 3.09 | 2.7 | 0.42 | 0.19 | 0.42 | 4.2 | 0.01 | ND | 0.03 | 0.17 |
| *A. pacificum* | CAWD049 | 2493 | 3.2 | 5.04 | 2.2 | 1.1 | 0.24 | 0.84 | 3.1 | 0.06 | ND | 0.12 | ND |
| *A. pacificum* | CAWD050 | 6310 | 0.43 | 1.09 | 0.38 | 0.07 | ND | 0.44 | 0.04 | ND | ND | 0.01 | 0.15 |
| *G. catenatum* | CAWD101 | 7788 | 0.49 | 170 | **48** | 8.4 | 3 | 1.3 | 0.25 | 0.02 | ND | 0.03 | 0.08 |
| *G. catenatum* | CAWD102 | 1953 | 1.3 | 9.3 | **85** | 3.2 | ND | 1.2 | 0.35 | 0.04 | ND | ND | 0.32 |
| *A. pacificum* | CAWD121 | 9027 | ND | ND | ND | 0.02 | ND | 0.01 | ND | 0.01 | ND | ND | ND |
| *G. catenatum* | CAWD126 | 17339 | 0.51 | 2.80 | **47** | 1.40 | 0.07 | 0.34 | 0.31 | 0.02 | 0.48 | ND | 0.08 |
| *A. ostenfeldii* | CAWD135 | 35571 | ND | 0.22 | ND | 0.02 | 0.77 | ND | ND | ND | ND | 0.02 | ND |
| *A. ostenfeldii* | CAWD136 | 2782 | ND | ND | ND | 0.07 | 0.49 | ND | ND | ND | ND | 0.01 | ND |
| *A. pacificum* | CAWD234 | 42662 | **5.6** | 3.25 | 1.6 | 0.18 | 0.17 | 1.5 | 0.2 | 0.04 | ND | 0.09 | 1.3 |
| *A. pacificum* | CAWD235 | 14680 | 1.5 | 2.88 | 1 | 0.2 | 0.14 | 2.5 | 0.13 | 0.09 | ND | 0.19 | 1.3 |
| *A. pacificum* | CAWD260 | 2136 | 0.06 | ND | ND | 0.09 | ND | 0.06 | ND | 0.02 | 0.05 | 0.01 | ND |
| *A. pacificum* | CAWD261 | 2502 | ND | ND | ND | 0.05 | ND | ND | ND | 0.01 | ND | ND | ND |
| *A. pacificum* | CAWD262 | 1227 | 3.4 | 3.12 | 0.54 | 1.8 | 0.22 | 1.6 | 0.12 | 0.27 | ND | 0.18 | 0.35 |

Gonyautoxin 1 (GTX1)
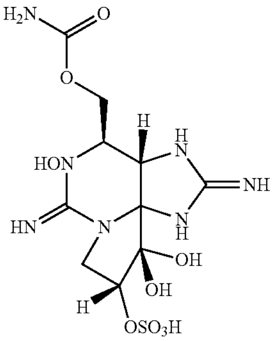
Gonyautoxin 2 (GTX2)
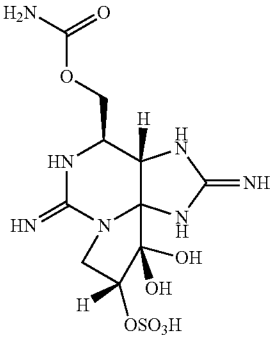
Gonyautoxin 3 (GTX3)
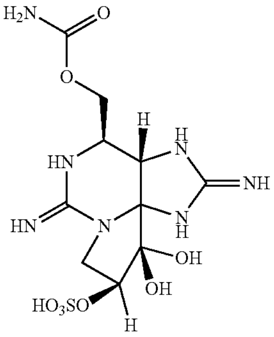
Gonyautoxin 4 (GTX4)
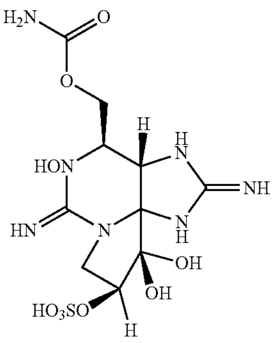
-continued
Gonyautoxin 5 (GTX5(B1))
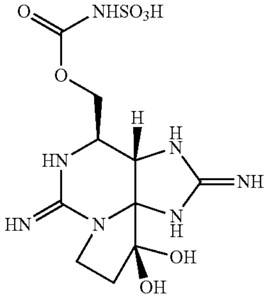
Gonyautoxin 6 (GTX6(B2))
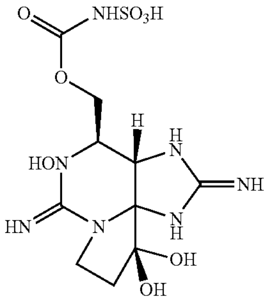
C1
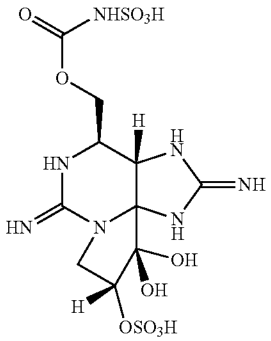
C2
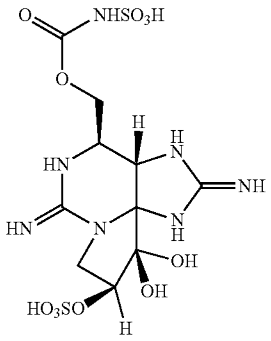
C3
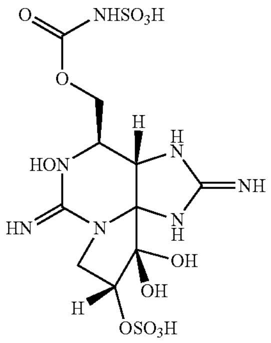

-continued

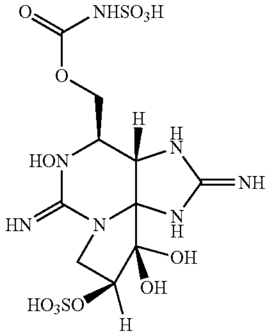

C4

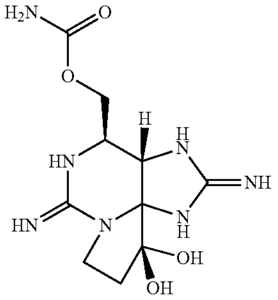

Saxitoxin (STX)

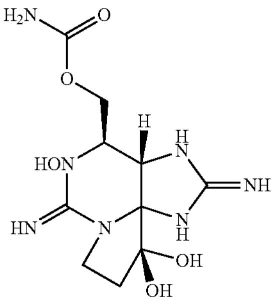

Neosaxitoxin (neoSTX)

A two-metre length (A+G) is dispensed from the tubular plastic roll and a hanging loop (2) formed at the first end. The hanging loop (2) is formed by folding back a 10 cm section (A) of the tubular plastic and heat welding together the four layers of plastic to provide a first heat weld (3) proximal to the cut first end. A second heat weld (4) is formed within the folded back section (A) parallel and spaced apart from the first heat weld (3) by about 2 cm followed by diagonal heat welds (5, 6) traversing the region between the horizontal first and second heat welds (3,4). The corners of the folded back section distal from the welds are then cut (7,8) to provide a hanging loop (2) of a width (B) capable of supporting the length of tubular plastic when filled with a volume of amended seawater.

The second end of the length of tubular plastic is sealed by double diagonal heat welds (9,10) converging to a point (11) proximal to the centre of the second end. The integrity of each double diagonal heat weld (9, 10) is inspected visually before each triangle of plastic outside the conical sealed end is cut (12, 13) away. The conical portion of the sealed end has a depth (C) of around 20 cm. Each hanging bag (1) is capable of containing a culture volume of approximately 24 L.

Prior to filling with inoculum and amended seawater a hanging bag (1) is hung in position and the top outside corner surface sterilised by wiping with isopropanol. A downward pointing first hole is formed in the surface sterilised region using a sterile pick. The tip of a sterilised air vent inserted into the hole and taped to the outside of the bag using PVC insulation tape (50 mm width). A region of the outer surface of the conical sealed end is also surface sterilised by wiping with isopropanol. A second hole is formed in the surface sterilised region using a sterile pick. The downward pointing tip of a sterile inoculation line is inserted into the hole and the line taped to the outside of the bag using PVC insulation tape (50 mm width).

Inoculum is fed into the hanging bag from a parent culture via the inoculation line. The line from the parent culture and the inoculation line to the hanging bag are each connected to a manifold. Air is purged from the lines by pumping amended seawater into both. The parent culture is then allowed to flow into the hanging bag. Pressurised air is introduced into the hanging bag containing the parent culture via its sterilised air vent. Equal volumes of the parent culture are transferred to multiple hanging bags. The inoculum containing hanging bags are then filled with the amended seawater to a fill line (D). Once the hanging bags are filled, the inoculation lines are disconnected from the manifold and connected to an air line via a sterilised air filter. The culture volume is aerated via the air line.

To monitor the pH of the medium during the culture the surface of a pH probe, including the glass bulb, is washed with deionised water and 70% (w/w) ethanol. A region of the outer surface of the hanging bag around 4 cm above the fill line is surface sterilised by wiping with isopropanol and a hole made in the bag within this region using a sterilised 10 mL pipette tip. The pH probe is inserted via the hole and into the culture volume and held flat against the inner side wall of the bag. Under these incubation conditions the isolates have a doubling time of about two days and are harvested when the cell density has reached $7\times10^4$ to $10^5$ cells/mL as determined by microscopic image cytometry.

D. Harvest

With aeration maintained the pH probe is removed and a volume of about 9 mL glacial acetic acid introduced into the culture volume. After about 10 to 20 minutes a volume of about 100 mL of a suspension of hydrated bentonite clay is added to the culture to provide a dosage of about 4 ml/L of culture. After a further 5 to 10 minutes the inoculation line is clamped and disconnected from the air filter. Settling of cells occurs over a period of time of at least 2 hours. The settled cells are drained into a centrifuge bottle and the collected volume (300 to 400 mL/bag) centrifuged in balanced bottles at a force of 1,500×g for a period of time of 5 minutes. The supernatant is discarded, and the harvested cells weighed before storing frozen at −20 °C.

E. Extraction

Extracts for (i) determining toxin profiles and monitoring toxin production, or (ii) preparation of C3,4 or GTX1,4 are prepared according to the following methods.

For monitoring toxin production, 10 mL of the culture volume is transferred to a polypropylene centrifuge tube and the cells pelleted by centrifugation at a force of 1,500×g for a period of time of 5 minutes. The supernatant is discarded, and the pellet resuspended in a volume of 250 μL 1 mM acetic acid. The volume is sonicated for a period of time of 2 minutes and heated to 80 °C for a period of time of 10 minutes. The cellular material is pelleted by centrifugation at a force of 3,220×g for a period of time of 5 minutes and 10-fold and 20-fold dilutions of the supernatant then prepared in 808 (v/v) acetonitrile/0.25% (v/v) acetic acid.

For preparation of C3,4 or GTX1,4 the frozen pellet of harvested cells is defrosted before resuspending in an equal volume of 0.58 acetic acid and leaving at room temperature for a period of time of 30 to 60 minutes. The suspension in acetic acid is then heated and maintained at a temperature of 85±2 °C in a water bath for a period of time of 10 to 15 minutes. The heated suspension is then cooled in an ice slurry before centrifugation at a force of 3,990×g for a period of time of 2 minutes and the first supernatant decanted to a collection vessel. An equal weight of 0.5% acetic acid is added to the pelleted cellular material, mixed well, and centrifuged at a force of 3,990×g for a period of time of 5 minutes. The second supernatant is decanted to the collection vessel and the total volume of collected supernatants reduced by rotary evaporation under vacuum (less than 15 mBar) at a temperature of 30 °C. (For example, portions of a total volume of 10 litres of supernatant are transferred from the collection vessel to a weighed 5 litre round bottom flask and the volume reduced by rotary evaporation until an extract having a weight of 800±50 g and a density between 1.08 to 1.12 g/mL is obtained.) The concentrated extract is stored frozen at −20 °C.

F. Analysis

A sample of extract is prepared for analysis using activated carbon solid phase extraction (SPE). A Supelclean™ ENVI-Carb™ SPE tube (bed wt. 250 mg, volume 6 mL) is conditioned with a volume of 3 mL of 20% acetonitrile/18 acetic acid followed by a volume of 3 mL of 0.025% ammonia. Following elution to the top frit the tube is loaded with a total volume of 400 μL consisting of 10 to 400 μL of extract and quantum sufficit deionised water. The cartridge is eluted to the top frit using a vacuum of −15 to −20 kPa and washed with a volume of 3 mL of deionised water before elution with a volume of 5 mL of 20% acetonitrile/1% acetic acid. The eluate is collected in a polypropylene tube and a volume of 10 uL diluted 4-fold with the addition of acetonitrile in a polypropylene autosampler vial. The contents of the vial are mixed on a vortex mixture with further dilution as required.

Method 1

Aqueous extracts and fractions enriched for the presence of C3,4 or GTX1,4 are analysed by high pressure liquid chromatography (HPLC) (Shimadzu Prominence) with ultraviolet (UV) detection according to this Method 1. Samples are diluted with 10 mM acetic acid to provide a nominal concentration of 200 μg/mL. A volume of 40 μL of diluted sample is injected onto a column (4.6×150 mm) of 3.5 μm Zorbax Bonus RP eluted with Mobile Phase A at a flow rate of 1 mL/min for a period of time of 30 minutes while being maintained at a temperature of 20 °C. The absorbance of the eluate is monitored at wavelengths of 210 nm (purity) and 245 nm (quantity) using a photodiode array detector (PAD). The purity of samples is calculated based on the percentage area at 210 nm and retention time with reference to a standard at a concentration of approximately 200 μg/mL C3,4 or GTX1,4. Samples are analysed in triplicate with 10 mM acetic acid used as a blank and the chromatogram obtained subtracted from that obtained for all samples.

Method 2

Extracts and fractions enriched for the presence of C3,4 or GTX1,4 are analysed and quantified by liquid chromatography-mass spectrometry (LC-MS) (Shimadzu 8050) according to this Method 2. Samples are diluted to an appropriate concentration using 80% acetonitrile/0.25% acetic acid. A mixed standard containing a number of reference paralytic shellfish toxins (PSTs) is used. A maximum volume of 2 μL of diluted sample is injected by means of an auto sampler maintained at 4 °C onto a column (2.1×100 mm) of 1.7 μM Waters Acquity UPLC BEH amide eluted at a flow rate of 0.4 mL/min while being maintained at a temperature of 20 °C. The column is eluted stepwise with 75% Mobile Phase B/25% Mobile Phase C for a period of time of 5 minutes following injection, followed by 55% Mobile Phase B/45% Mobile Phase C for a period of time of 0.50 min before reverting to 75% Mobile Phase B/25% Mobile Phase C. The eluate is monitored by mass spectrometry using selective ion monitoring in ESI− and ESI+ ionisation modes.

Method 3

Purified products of extraction, fractionation and conversion are analysed for quantity and purity according to this Method 3. Isolated products (C3,4 or GTX1,4 or GTX6 or neoSTX) are diluted to a concentration of 200 μg/mL in 10 mM acetic acid. The diluted sample is then further diluted 100-fold in 8% acetonitrile/0.25% acetic acid to provide a solution of product at a concentration of 20 mg/mL for quantitative analysis. A mixed standard containing a number of reference paralytic shellfish toxins (PSTs) is also prepared in the same solvent. A solution of 2 μL of the diluted product (20 ng/mL) is injected by means of an autosampler maintained at a temperature of 40 °C onto a column (2.1×100 mm) of 1.7 μm Waters Acquity UPLC BEH amide eluted at a flow rate of 0.6 mL/min while being maintained at a temperature of 60 °C. The column is eluted stepwise with 80% Mobile Phase B/20% Mobile Phase C for a period of time of 6 minutes following injection, followed by 55% Mobile Phase B/45% Mobile Phase C for a period of time of 0.50 minutes before reverting to 80% Mobile Phase B/20% Mobile Phase C. The eluate is monitored by mass spectrometry monitoring in ESI− and ESI+ ionisation modes.

G. Enrichment

The concentrated extract is thawed at room temperature. The extract is divided between two balanced 500 ml conical centrifuge bottles and centrifuged at a force of 4000×g for a period of time of 10 minutes. The supernatant is decanted and filtered under reduced pressure through a series of 110 mm diameter hardened ashless and glass microfiber filter papers (Whatman™ grade 540, Whatman™ grade 542 and Whatman™ grade GF/A). The filtered extract is then subjected to crossflow ultrafiltration by recirculation through two filters (VivaFlow 200) connected in parallel with an outlet pressure no greater than 2.5 bar until the volume of the extract has been reduced to a volume of 10 to 20 mL of retentate.

For the enrichment of GTX1,4 or C3,4 from extracts of cultures of isolates of *Alexandrium pacificum* or *Gymnodinium catenatum*, respectively, the retentate is transferred to a 100 ml bottle and made up to a total volume of 100 mL with deionised water. The diluted retentate is similarly subjected to rounds of crossflow ultrafiltration reducing the volume of retentate to 10 to 20 mL before making up to a total volume of 100 mL with deionised water.

For the enrichment of GTX1,4 from extracts of cultures of isolates of *Gymnodinium catenatum* the retentate is transferred to a 100 ml bottle and made up to a total volume of 100 mL with dilute hydrochloric acid to provide a final concentration of 0.1 N HCl. The acidified, diluted retentate is then heated and maintained at a temperature of 80 °C±2 °C in a water bath for a period of time of at least 30 minutes. The acidified, diluted retentate is then cooled in an ice slurry, neutralised with ammonium hydroxide, and similarly subjected to rounds of crossflow ultrafiltration reducing the volume of retentate to 10 to 20 mL before making up to a total volume of 100 mL with deionised water.

A 32 mm 5 μm syringe filter (Pall Corp.) is installed on the inlet of a 50 g Sepabeads™ SP-270 (Supelco) SPE cartridge conditioned with 500 mL of deionised water at a flow rate of 30 mL/minute. The washed retentate is passed through the conditioned SPE cartridge at a flow rate of 30 mL/minute and the effluent collected. The SPE cartridge is then eluted with 200 mL of deionised water at a flowrate of 30 mL/minute and the effluent collected. The volume of the combined effluents is reduced by rotary evaporation under vacuum (less than 15 mBar) at a temperature of 30±2 °C. The volume is reduced to provide a weight of 500±50 g, the density determined gravimetrically, and the total reduced volume calculated on this basis. Prior to purification of the C3,4 or GTX1,4 or GTX6 from the reduced volume on a preparative scale a sample of the reduced volume is prepared and analysed as described (F. Analysis). A 10,000-fold dilution of the sample should provide a concentration of C3,4 or GTX1,4 or GTX6 in the range 20 to 50 ng/mL.

H. Purification

The total reduced volume is desalted by loading on a 100 g 25×450 mm carbon column (Enviro-Clean™ Graphitized Carbon Non-Porous, UCT) conditioned with 1 L of deionised water. The reduced volume is loaded at a flow rate of 30 ml/min using a Mini-Flash Pump (Sorbent Technologies, Inc.) and eluted at a flow rate of 15 ml/min with a stepwise gradient of deionised water for a period of time of 40 minutes followed by 0.2% (v/v) acetic acid/30% (v/v) acetonitrile for a period of time of 40 minutes.

The eluate is monitored at 205 nm using an inline UV detector and sequential volumes of 10 mL of eluate collected as fractions. Volumes of 5 μL of selected fractions are diluted to a total volume of 10 mL with 0.25% (v/v) acetic acid/80% (v/v) acetonitrile and submitted to LC-MS analysis as described (F. Analysis). The C3,4 or GTX1,4 or GTX6 containing fractions are combined.

The pH of the desalted combined fractions collected from the carbon column is adjusted to 7.8 using concentrated ammonium hydroxide at a rate of approximately 2 μL/mL. The pH adjusted volume is then loaded on a 35×460 mm column of 280 g Sepra™ WCX-$NH_4^+$ conditioned using a volume of 1 L of 50 mM ammonium bicarbonate at a flow rate of 30 ml/min. The column is eluted with a gradient of 10 to 80% 0.5 M ammonium bicarbonate over a period of time of 100 minutes. The eluate is monitored at wavelengths of 205 nm and 245 nm using an inline UV detector. Sequential volumes of 25 ml are collected as fractions and combined according to the UV monitoring and LC-MS analysis where required (F. Analysis). Fractions containing greater than 28 of the total amount of C3,4 or GTX1,4 or GTX6 are combined and the pH of the combined fractions reduced to 6.5 by the dropwise addition of glacial acetic acid. A 5,000-fold dilution of the acidified volume is subjected to LC-MS analysis as described (F. Analysis). For GTX1,4 the total quantity and yield and ratio to GTX5 is calculated. The yield should be greater than 90% and the ratio of GTX5 to GTX 1,4 should be less than 18. For C3,4 the total quantity and yield and ratio to GTX6 is calculated. The yield should be greater than 90% and the ratio of GTX6 to C3,4 should be less than 1%.

The combined fractions from the weak cation exchange chromatography are loaded onto a 35×480 mm column of 175 g Sepra™ ZT-WCX-$H^+$ form conditioned using 1 L of deionised water at a flowrate of 30 mL/min. The loaded column is eluted with a continuous gradient of 0 to 100% 1M acetic acid in water over a period of time of 100 minutes and sequential volumes of 25 mL of eluate collected as fractions while monitoring at a wavelength of 205 nm using an inline UV detector. The C3,4 or GTX1,4 or GTX6 containing fractions are collected from baseline to baseline and the total volume reduced to a volume of 10 to 20 mL by rotary evaporation at 30 °C under reduced pressure of less than 15 mBar. A 500,000-fold dilution of the reduced volume is subjected to LC-MS analysis as described (F. Analysis) and the total quantity and yield of C3,4 or GTX1,4 or GTX6 calculated on this basis.

The C3,4 or GTX1,4 or GTX6 containing reduced volume is loaded on a 50×500 mm column of P2 gel conditioned with 2 L of 100 mM acetic acid at a flowrate of 50 mL/min and eluted isocratically with the same conditioning mobile phase. The eluate is monitored at a wavelength of 205 nm for a period of time of 200 minutes using an inline UV detector and sequential volumes of 10 mL of eluate collected as fractions. The C3,4 or GTX1,4 or GTX6 containing fractions are collected from baseline to baseline and the total volume reduced by rotary evaporation at a temperature of 30 °C under reduced pressure of less than 15 mBar.

The reduced volume of combined fractions obtained by gel filtration is transferred to a pre-weighed 100 mL round bottom flask and evaporated to dryness by rotary evaporation at a temperature of 30 °C under a reduced pressure of less than 15 mbar followed by drying in a freeze dryer at a shelf temperature of 10 °C and pressure of 0.05 mbar for 24 hours. The open mouth of the round bottom flask is securely covered with an air permeable, lint free tissue before placing in the freeze dryer. The yield of purified C3,4 or GTX1,4 or GTX6 is determined gravimetrically. The purified C3,4 or GTX1,4 or GTX6 is dissolved in a known volume of deionised water to provide a solution containing 70 to 100 mg/ml of C3,4 or GTX1,4 or GTX6.

A 500-fold dilution of the solution in 10 mM acetic acid is prepared and analysed as described (F. Analysis). The final volume required to provide a concentration of 40 to 45 mg/mL of C3,4 or GTX1,4 or GTX6 is calculated and the solution transferred via a filter to a pre-weighed 10 mL amber glass vial, rinsing with deionised water to provide a transferred volume having the target concentration of 40 to 45 mg/mL. A 200-fold dilution of the transferred solution is prepared in 10 mM acetic acid and analysed as described (F. Analysis). The dilution is diluted a further 10-fold in 10 mM acetic acid and analysed for purity as described (F. Analysis).

I. Conversion of GTX1,4 to neoSTX

Figure 4:
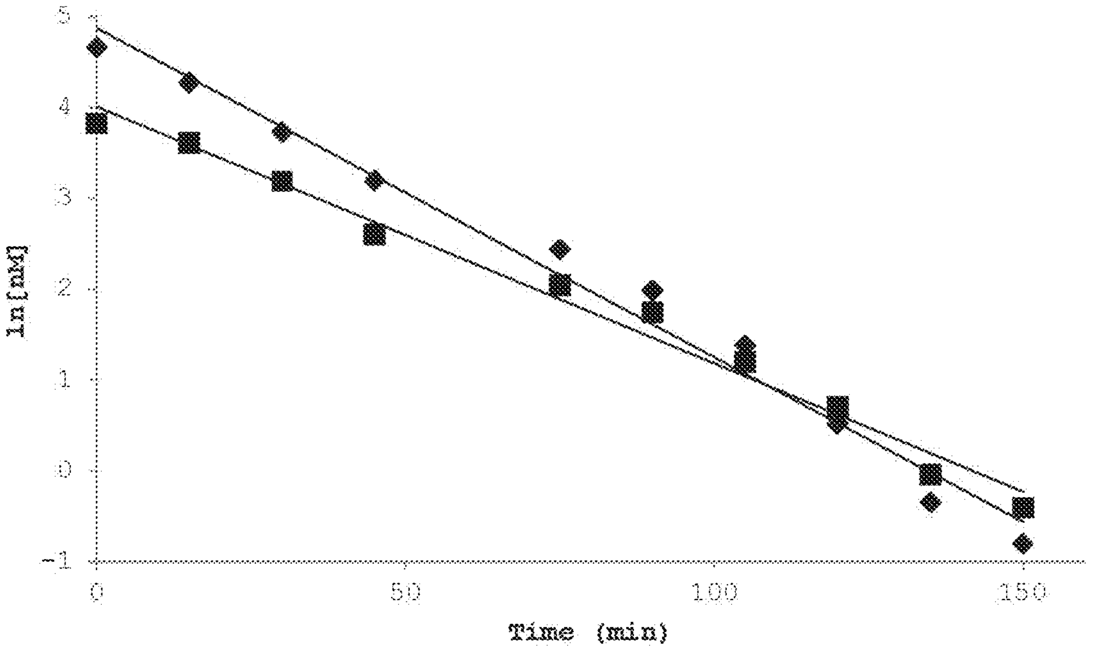
FIG. 4. Plot of concentration of gonyautoxins (GTX 1 (♦) and GTX 4 (■)) versus time during reductive sulfonation with dithiothreitol (DTT).

A quantity of 183 mg (as the free base) of GTX1,4 purified according to the preceding steps from an extract of a culture of the isolate of *Alexandrium pacificum* designated CAWD234 is dissolved in a total volume of 5 mL of dilute acetic acid and mixed with a volume of 45 mL of 0.2 M phosphate buffer at a pH of 7.5 in a 100 mL round bottom flask. The mixture is placed on ice and the pH adjusted from 6.8 to 7.5 with the addition whilst stirring of solid sodium carbonate. A quantity of 1.5 g of dithiothreitol (DTT) is added to the pH adjusted mixture and its dissolution promoted by placing the reaction mixture containing round bottom flask in an ultrasonic bath before transferring to a water bath maintained at a temperature of 50 °C. Aliquots of a volume of 10 μL are removed from the reaction mixture and transferred to the water bath (T=0) and periodically (every 15 minutes) thereafter. Aliquots are diluted 50-fold by the addition of a volume of 490 μL 80% acetonitrile 0.25% acetic acid immediately following removal from the reaction mixture and analysed by LC-MS as described (F. Analysis) to monitor the progress of the reaction in near real time (FIG. 4). After incubation for 45 minutes at 50 °C the reaction mixture is chilled by transferring the round bottom flask to a ice slurry. Under these conditions near quantitative conversion of GTX1,4 to neoSTX is observed with close to 100% yield.

J. Conversion of C3, 4 to GTX6

Analytical Scale

Preliminary studies were performed to confirm the viability of the proposed conversion of C3,4 to GTX6. A volume of 400 μL of phosphate buffer (pH 7.3) at a concentration of 200 mM and a volume of 9.6 μL of a solution of dithiothreitol (DTT) at a concentration of 421 mM were added to a volume of 100 μL of a solution of C3,4 at a concentration of 3.6 mM to provide a reaction mixture containing molar equivalents in the ratio 20:10:1.

The reaction mixture was heated in a water bath to a temperature of 50 °C for a period of time of 60 minutes before being cooled in ice water to provide a solution of reaction product. A volume of 10 μL of the solution of reaction product was diluted 10,000-fold with 80% (v/v) acetonitrile/0.25% acetic acid and analysed [F. Analysis].

TABLE 2

Calculation of yield of GTX6.

| | Concentration (μg/mL) | |
|---|---|---|
| Toxin | 0 | 60 min |
| C3, 4 | 354 | — |
| GTX6 | — | 238 |

A yield of 67% (w/w) was obtained (Table 2), i.e., a molar yield of greater than 80%. It is anticipated that further improvements in yield and reduced reaction times (less than one hour) will be achievable when using higher concentrations (greater than 80 mM of C3,4). Reduced reaction times are also anticipated to reduce the formation of decarbamoylneosaxitoxin (dcNEO) attributed to the hydrolysis of GTX6 at the elevated pH of the reaction mixture.

Preparative Scale

In a proposed method a quantity of 183 mg (as the free base) of C3,4 purified according to the preceding steps from an extract of a culture of an isolate of *Gymnodinium catenatum* is dissolved in a total volume of 5 mL of dilute acetic acid and mixed with a volume of 45 mL of 0.2 M phosphate buffer at a pH of 7.5 in a 100 mL round bottom flask. The mixture is placed on ice and the pH adjusted from 6.8 to 7.5 with the addition whilst stirring of solid sodium carbonate. A quantity of 1.5 g of dithiothreitol (DTT) is added to the pH adjusted mixture and its dissolution promoted by placing the reaction mixture containing round bottom flask in an ultrasonic bath before transferring to a water bath maintained at a temperature of 50 °C. Aliquots of a volume of 10 μL are removed from the reaction mixture and transferred to the water bath (T=0) and periodically (every 15 minutes) thereafter. Aliquots are diluted 50-fold by the addition of a volume of 490 μL 80% acetonitrile 0.25% acetic acid immediately following removal from the reaction mixture and analysed by LC-MS as described (F. Analysis) to monitor the progress of the reaction in near real time. After incubation for 45 minutes at 50 °C the reaction mixture is chilled by transferring the round bottom flask to an ice slurry.

K. Isolation of neoSTX

The product from the conversion of GTX1,4 to neoSTX is loaded onto a quantity of 39 g Sepra™ WCX packed in an empty flash cartridge (Grace) and preconditioned with a volume of 250 mL of 50% (w/w) acetonitrile followed by a volume of 250 mL of deionised water. The conversion product is loaded onto the packed cartridge with rinses of deionised water with collection of the effluent (about 200 mL). The dissolution of any crystals formed during storage of the conversion product at 4 °C is achieved by the addition of a minimal amount of deionised water. The loaded packed cartridge is then eluted at a rate of 50 mL/min with a total volume of 1.5 L, followed by elution with a continuous gradient to 1 M acetic acid over 20 minutes and the collection of sequential volumes of 10 mL of eluate as fractions while monitoring UV absorbance at 205 nm and 254 nm.

A volume of 5 μL of fractions demonstrating UV absorbance at 205 nm is diluted 100,000-fold in 80% acetonitrile 0.25% acetic acid and analysed by LC-MS. Fractions confirmed to comprise neoSTX are combined, frozen at −70 °C and lyophilised. The dried neoSTX is dissolved in a small volume of 10 mM and transferred to a pre-weighed 10 mL glass vial and a volume of 10 μL analysed. The purity and quantity of a batch (CNC00063) of neoSTX prepared according to the foregoing method is provided in Table 3.

TABLE 3

Specification for a batch (CNC00063) of neoSTX prepared according to the semisynthetic method described.

| Component | Quantity (mg) | % (w/w) |
|---|---|---|
| neoSTX | 118 | 99.58 |
| L-arginine | 0.444 | 0.37 |
| STX | 0.0546 | 0.05 |
| DTT | <0.005 | <0.004 |
| TOTAL | 119 | 100 |

It is proposed that GTX6 may be similarly purified from the product of the conversion of C3,4 to GTX6 and then subjected to mild acid hydrolysis to provide neoSTX (Shimizu (1984)).

L. Conversion of GTX6 to neoSTX

According to this proposed method the product from the conversion of C3,4 to GTX6 is loaded onto a quantity of 39 g Sepra™ WCX packed in an empty flash cartridge (Grace) and preconditioned with a volume of 250 mL of 50% (w/w) acetonitrile followed by a volume of 250 mL of deionised water. The conversion product is loaded onto the packed cartridge with rinses of deionised water with collection of the effluent (about 200 mL). The dissolution of any crystals formed during storage of the conversion product at 4 °C is achieved by the addition of a minimal amount of deionised water. The loaded packed cartridge is then eluted at a rate of 50 mL/min with a total volume of 1.5 L, followed by elution with a continuous gradient to 1 M acetic acid over 20 minutes and the collection of sequential volumes of 10 mL of eluate as fractions while monitoring UV absorbance at 205 nm and 254 nm.

A volume of 5 μL of fractions demonstrating UV absorbance at 205 nm is diluted 100,000-fold in 80% acetonitrile 0.25% acetic acid and analysed by LC-MS.

Fractions confirmed to comprise GTX6 are combined, frozen at −70 °C and lyophilised. The dried GTX6 is dissolved in a small volume of 10 mM and transferred to a pre-weighed 10 mL glass vial and a volume of 10 μL analysed.

Analytical Scale

Preliminary studies were performed to confirm the viability of the proposed conversion of GTX6 to neosaxitoxin. A volume of 2 μL of concentrated hydrochloric acid (HCL) was added to a volume of 118 μL of a solution of GTX6. The acidified solution (0.2M HCl, pH 0.97) was then heated in a boiling water bath for a period of time of 10 minutes before cooling in iced water.

A volume of 10 μL of the cooled acidified solution was diluted 1,000-fold with 80% (v/v) acetonitrile/0.25% acetic acid and analysed [F. Analysis].

TABLE 4

Calculation of yield of neosaxitoxin.

| Toxin | Concentration* (μg/mL) 0 min | 60 min |
|---|---|---|
| GTX6 | 16.74 | — |
| Neosaxitoxin | — | 14.05 |

(*Mean of duplicate samples.)

A yield of 84% (w/w) was obtained (Table 4), i.e., a qualitative conversion of GTX6 to neosaxitoxin.

Preparative Scale

In the proposed batch preparation of neosaxitoxin larger amounts of purified GTX6 are subjected to mild acid hydrolysis by dissolving in a volume of 1N HCl in a round bottom flask and heating to 80 °C for at least 30 min. The hydrolysate is chilled by transferring the round bottom flask to an ice slurry. The pH of the cooled acidified solution is adjusted to about 6.6 before being loaded onto a Sepra™ WCX column and eluting with approximately three column volumes of water followed by approximately five column volumes of 1 M acetic acid. Neosaxitoxin containing fractions are combined and evaporated to dryness before being transferred to a final vessel in 0.1% (w/v) acetic acid. The neosaxitoxin may then be similarly isolated from the hydrolysate (K. Isolation).

REFERENCED PUBLICATIONS

Baker et al (2003) *GTX4 imposters: characterization of fluorescent compounds synthesized by Pseudomonas stutzeri SF/PS and Pseudomonas/Alteromonas PTB-b* 1, *symbionts of saxitoxin-producing Alexandrium spp.* Toxicon, 41(3), 339-347.

Balech (1995) The *genus Alexandrium Halim* (*Dinoflagellata*) Sherkin Island Marine Station, Sherkin Island, Ireland 151 pp.

Beach et al (2018) *Capillary electrophoresis-tandem mass spectrometry for multiclass analysis of polar marine toxins* Analytical and Bioanalytical Chemistry, 410 (22), 5405-5420.

Bernardi Bif et al (2013) *Evaluation of mysids and sea urchins exposed to saxitoxins* Environmental Toxicology and Pharmacology, 36(3), 819-825.

Chen et al (2016) *Simultaneous screening for lipophilic and hydrophilic toxins in marine harmful algae using a serially coupled reversed-phase and hydrophilic interaction liquid chromatography separation system with high-resolution mass spectrometry* Analytica Chimica Acta, 914, 117-126.

Cho et al (2016) *Column switching combined with hydrophilic interaction chromatography-tandem mass spectrometry for the analysis of saxitoxin analogues, and their biosynthetic intermediates in dinoflagellates* Journal of Chromatography A, 1474, 109-120.

Daigo et al (1985) *Isolation and some properties of neosaxitoxin from a xanthid crab Zosimus aeneus* Nippon Suisan Gakkaishi, 51(2), 309-13.

Foss et al (2012) *Investigation of extraction and analysis techniques for Lyngbya wollei derived Paralytic Shellfish Toxins* Toxicon, 60(6), 1148-1158.

Garcia-Altares (2017) *Structural diversity of microalgal marine toxins* Comprehensive Analytical Chemistry, 78, 35-75.

Hall et al (1984) *Dinoflagellate neurotoxins related to saxitoxin: structures of toxins C3 and C4, and confirmation of the structure of neosaxitoxin*

Jiang and Jiang (2008) *Investigation of extraction method for paralytic shellfish poisoning toxins in shellfish* Fenxi Huaxue, 36(11), 1460-1464.

Kellmann and Neilan (2007) Fermentative production of neosaxitoxin and its analogs in recombinant Escherichia coli strains International application no. PCT/EP2017/053077 [publ. no. WO 2017/137606 A1].

Lagos Gonzáles (2010) Methods for purifying phycotoxins, pharmaceutical compositions containing purified phycotoxins, and methods of use thereof International application nos. PCT/IB2010/051187 [publ. no. WO 2010/109386 A1] and PCT/IB2010/051188 [publ. no. WO 2010/109387 A1].

Lagos Gonzáles (2015a) Methods for producing phycotoxins U.S. Pat. No. 8,957,207 B2.

Lagos Gonzáles (2015b) Methods for purifying phycotoxins, pharmaceutical compositions containing purified phycotoxins and methods of use thereof U.S. Pat. No. 8,952,152 B2.

Lagos Gonzáles (2016) Methods for purifying phycotoxins, pharmaceutical compositions containing purified phycotoxins and methods of use thereof U.S. Pat. No. 9,249,150 B2.

Laycock et al (1994) *Isolation and purification procedures for the preparation of paralytic shellfish poisoning toxin standards* Natural Toxins, 2(4), 175-83.

Laycock et al (1995) *Some in vitro chemical interconversions of paralytic shellfish poisoning (PSP) toxins useful in the preparation of analytical standards* Journal of Marine Biotechnology (Proceedings of the Third International Marine Biotechnology Conference, 1994), 3(1-3), 121-125.

Li et al (2013) *Rapid screening, identification of paralytic shellfish poisoning toxins in red tide algae using hydrophilic interaction chromatography-high resolution mass spectrometry with an accurate-mass database* Fenxi Huaxue, 41(7), 979-985.

Liu et al (2010) *Cultivation of Alexandrium catenella and extraction and detection of paralytic shellfish poisoning toxins* Shuichan Xuebao, 34(11), 1783-1788.

Mezher (2018) *FDA to replace analgesic drug development guidance with new documents* Regulatory Focus News Article (www.raps.org/news-and-articles/news-articles/2018/8/fda-2-replace-analgesic-drug-development-guidance).

Miao et al (2004) *Isolation and purification of gonyautoxins from two strain of Alexandrium minutum Halim* Journal of Chinese Pharmaceutical Sciences, 13(2), 103-105.

Parker et al (2002) *Growth of the toxic dinoflagellate Alexandrium minutum (Dinophyceae) using high biomass culture systems* Journal of Applied Phycology, 14(5), 313-324.

Poyer et al (2015) *Identification and separation of saxitoxins using hydrophilic interaction liquid chromatography coupled to traveling wave ion mobility-mass spectrometry* Journal of Mass Spectrometry, 50(1), 175-181.

Ravn et al (1995) *Standardized extraction method for paralytic shellfish toxins in phytoplankton* Journal of Applied Phycology, 7(6), 589-94.

Rubio et al (2015) *Purification and characterization of saxitoxin from Mytilus chilensis of southern Chile* Toxicon, 108, 147-153.

Sakamoto et al (2000) *Formation of intermediate conjugates in the reductive transformation of gonyautoxins to saxitoxins by thiol compounds* Fisheries Science, 66, 136-141.

Sato et al (2000) *Identification of thioether intermediates in the reductive transformation of gonyautoxins into saxitoxins by thiols* Bioorganic and Medicinal Chemistry Letters 10, 1787-1789.

Shimizu (1984) *Paralytic shellfish poisons In Fortschritte der Chemie organischer Naturstoffe/Progress in the Chemistry of Organic Natural Products* Herz et al (Springer-Verlag, Wien).

Siu et al (1997) *Environmental and nutritional factors which regulate population dynamics and toxin production in the dinoflagellate Alexandrium catenella* Hydrobiologia, 352, 117-140.

Suzuki et al (2014) *Preparation of diarrhetic shellfish toxins (DSTs) and paralytic shellfish toxins (PSTs) by large algal culture and chemical conversion* A. Lincoln Mackenzie [Ed]. Marine and Freshwater Harmful Algae, Proceedings of the 16$^{th}$ International Conference on Harmful Algae. Cawthron Institute, Nelson, New Zealand and the International Society for the Study of Harmful Algae (ISSHA).

Tsai et al (1997) *Toxicity and toxic components of two xanthid crabs, Atergatis floridus and Demania reynaudi, of Taiwan* Toxicon, 35(8), 1327-1335.

Wang et al (2010) Paralytic shellfish poison or PSP standard substances and preparations for monitoring sea food industries Chinese patent application no. 2010-10179534 [publ. no. CN 101858833 A].

The invention claimed is:

1. A batch preparation comprising greater than 100 mg of neosaxitoxin at a purity of 99.5% (w/w) and no greater than 0.05% (w/w) saxitoxin.

2. The batch preparation of claim 1 comprising less than 0.004% (w/w) dithiotreitol.

3. The batch preparation of claim 2 comprising no greater than 0.37% (w/w) L-arginine.

* * * * *